United States Patent
Min

(10) Patent No.: US 10,524,683 B2
(45) Date of Patent: Jan. 7, 2020

(54) EEG-BASED BRAIN-MACHINE INTERFACE APPARATUS AND METHOD FOR RECOGNIZING HUMAN-INTENTION USING FLICKERING VISUAL STIMULUS

(71) Applicant: Korea University Research and Business Foundation, Seoul (KR)

(72) Inventor: Byoung-Kyong Min, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 521 days.

(21) Appl. No.: 14/884,972

(22) Filed: Oct. 16, 2015

(65) Prior Publication Data

US 2016/0192858 A1     Jul. 7, 2016

Related U.S. Application Data

(63) Continuation-in-part of application No. PCT/KR2013/008194, filed on Sep. 11, 2013.

(30) Foreign Application Priority Data

Apr. 16, 2013  (KR) .......................... 10-2013-0041829
Jul. 27, 2015  (KR) .......................... 10-2015-0106073

(51) Int. Cl.
  *A61B 5/0484*  (2006.01)
  *A61B 5/0482*  (2006.01)
  *A61B 5/00*    (2006.01)

(52) U.S. Cl.
  CPC ........ *A61B 5/04842* (2013.01); *A61B 5/0482* (2013.01); *A61B 5/7264* (2013.01); *A61B 5/742* (2013.01)

(58) Field of Classification Search
  None
  See application file for complete search history.

(56) References Cited

U.S. PATENT DOCUMENTS

| | | | |
|---|---|---|---|
| 2010/0092934 A1* | 4/2010 | Silberstein ......... | A61B 5/04008 434/236 |
| 2011/0040202 A1* | 2/2011 | Luo .................... | A61B 5/04842 600/544 |

FOREIGN PATENT DOCUMENTS

| | | |
|---|---|---|
| CN | 102654793 A | 9/2012 |
| JP | 2001-184027 A | 7/2001 |

(Continued)

OTHER PUBLICATIONS

Zhang et al., Multiple Frequencies Sequential Coding for SSVEP-Based Brain-Computer Interface, PLoS ONE 7(3):e29519, 2012.*

(Continued)

*Primary Examiner* — David J. McCrosky
*Assistant Examiner* — Jay B Shah
(74) *Attorney, Agent, or Firm* — Fox Rothschild LLP

(57) ABSTRACT

A brain-machine interface apparatus and a method of the same are provided. To elaborate the brain-machine interface apparatus may include a display where a plurality of light-emitting points (or lines) flickering with their individual set frequencies are arranged a flickering controller that divides the plurality of the light-emitting points (or lines) into a plurality of groups, and sets the set frequencies for the groups; an EEG measurement unit that detects EEG signals of a user who watches the display without gaze-shift; a frequency detector that detects one or more (their harmonic or combination) frequency components from the measured EEG signals; a shape analysis unit that decodes an originally intended shape according to the user's imagination based on the one or more detected frequency components and the set frequencies; and a result output unit that outputs information of the embodied originally intended shape.

18 Claims, 10 Drawing Sheets

(56) References Cited

FOREIGN PATENT DOCUMENTS

| KR | 10-0913753 | B1 |   | 8/2009 |
|----|------------|----|---|--------|
| KR | 10-1034875 | B1 |   | 5/2011 |
| KR | 2013-0002590 | A |   | 1/2013 |
| KR | 101285821 | B1 | * | 7/2013 |
| KR | 1020140137870 | A |   | 12/2014 |
| KR | 1020150078811 | A |   | 7/2015 |
| WO | 2012029742 | A1 |   | 3/2012 |

OTHER PUBLICATIONS

International Search Report for PCT/KR2013/008194 dated Nov. 25, 2013.

* cited by examiner

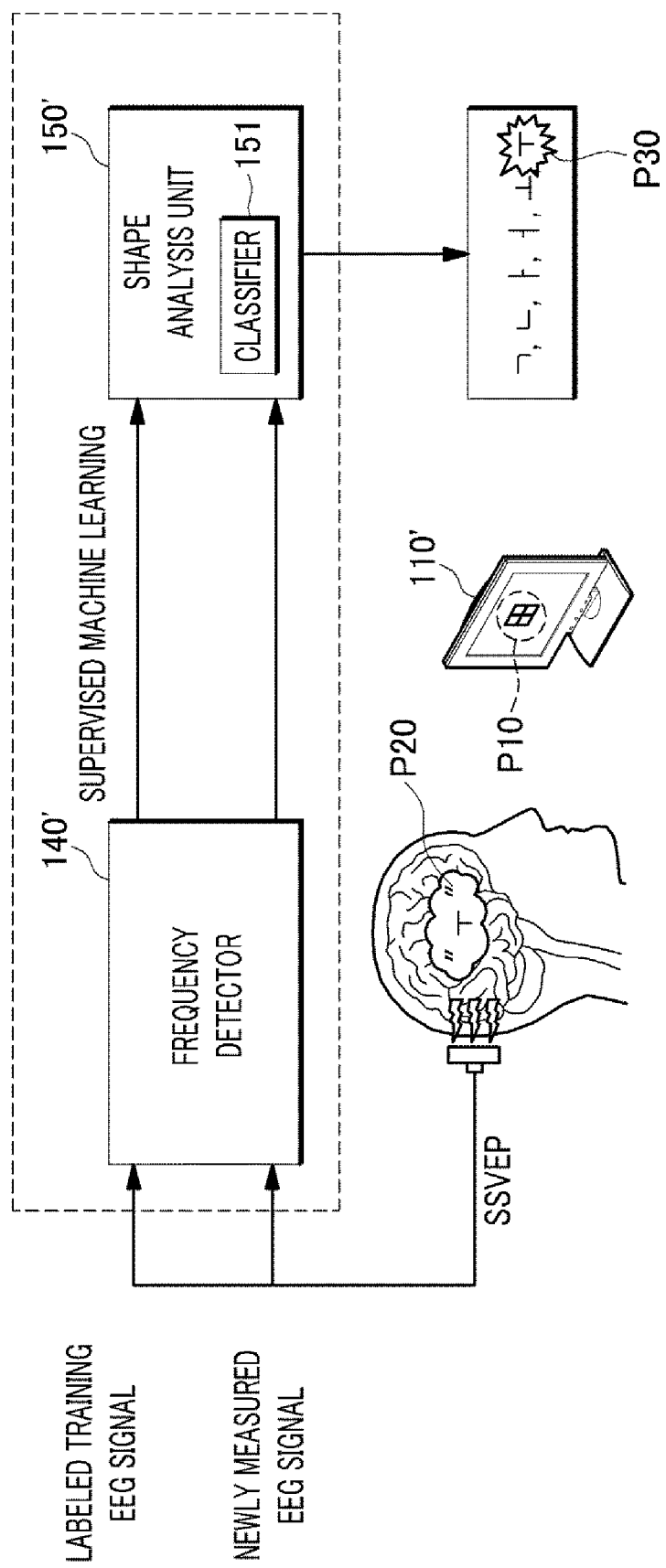

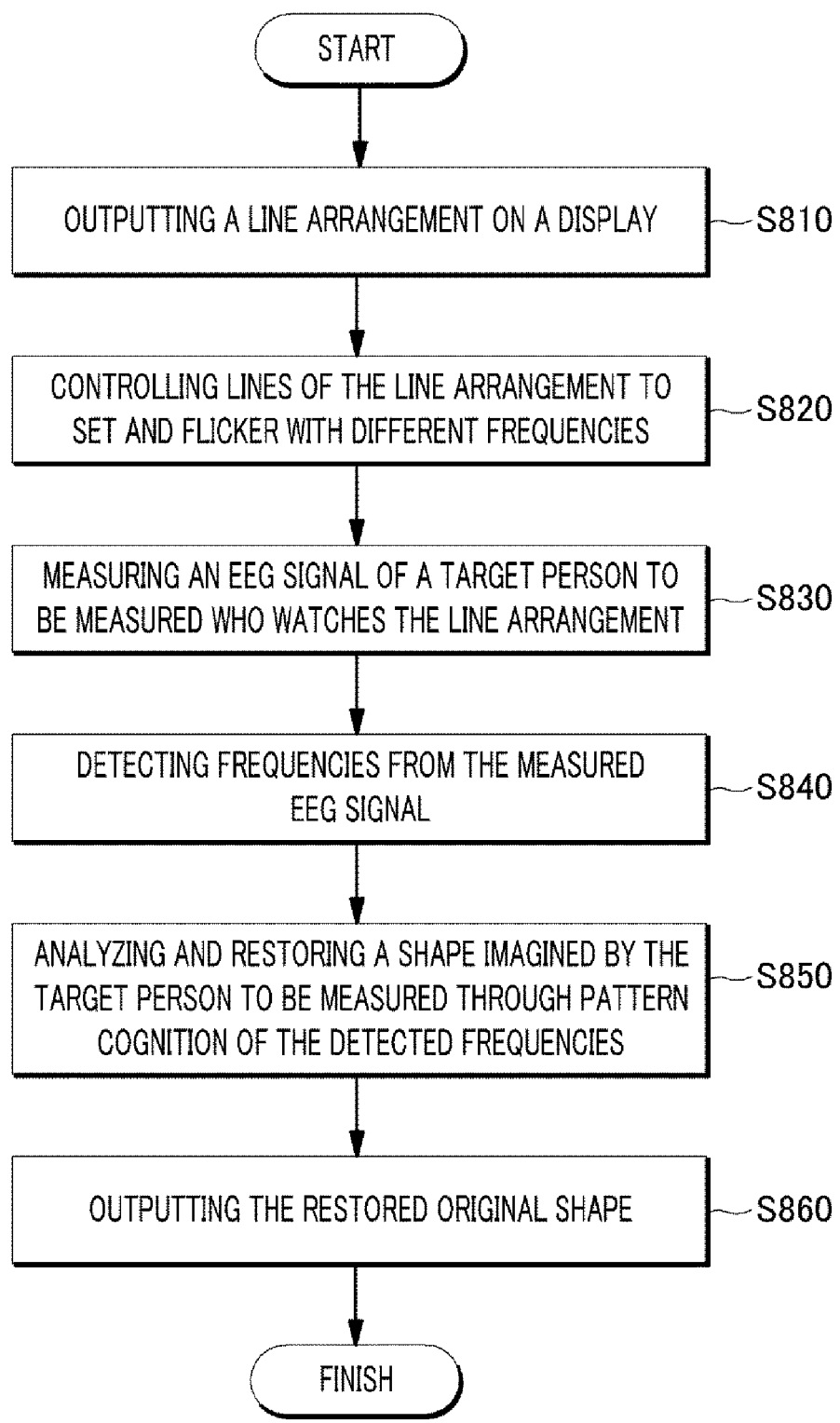

US 10,524,683 B2

EEG-BASED BRAIN-MACHINE INTERFACE APPARATUS AND METHOD FOR RECOGNIZING HUMAN-INTENTION USING FLICKERING VISUAL STIMULUS

CROSS-REFERENCE TO RELATED PATENT APPLICATION

This application claims priority from the Korean Patent Application No. 10-2013-0041829, filed on Apr. 16, 2013, the PCT Patent Application No. PCT/KR2013/008194 filed on Sep. 11, 2013, and the Korean Patent Application No. 10-2015-0106073, filed on Jul. 27, 2015, the entire disclosure of which is incorporated herein by reference in its entirety.

STATEMENT REGARDING THIRD PARTY RESEARCH PROJECT

This work was supported by the Basic Science Research Program (2015R1A1A1A05027233) of the National Research Foundation of Korea (NRF) funded by the Ministry of Science, ICT and Future Planning.

TECHNICAL FIELD

The embodiments described herein pertain generally to an apparatus and a method for processing brain-machine interface (BMI) by using an electroencephalogram (EEG) signal depends on a visual stimulus.

BACKGROUND

In order to control brain-machine interface according to intention of a person by using an EEG signal, parameters for cognitive properties of brainwaves are analyzed and used.

When an EEG signal is used as an interface control signal as described above, the EEG signal can be analyzed by an analytic method based on a time or frequency axis. In this case, the analysis method based on the time axis repeatedly measures an EEG signal associated with stimulus presentation, to arrange unit EEG segments relative to the time point of the stimulus onset, and then, calculate an average EEG potentials based on the stimulus-onset time point. This method uses the principle that only the EEG signal associated with the stimulus (or event) is effective for the average value and survives after averaging, and an EEG signal irrelevant to the stimulation is canceled out by the average.

A brain potential, which is obtained by being accumulated from an average value in relation to a presentation of a stimulus or an event, is called an 'event-related potential (ERP).' With respect to a representative EEG component obtained by the EEG analysis based on the time axis, there is a 'steady state visual evoked potential (SSVEP).' The SSVEP component is an EEG signal using EEG responding to repeatedly flickering visual stimuli. For example, when a person watches a flickering stimulus, a spectral EEG component at the same frequency as the flickering-stimulus frequency is physically driven. In this case, the oscillatory EEG activity, which is induced by the flickering visual stimulus and has the same frequency as that of the stimulus, corresponds to SSVEP.

In this regard, Korean Patent Application Publication No. 2013-0002590 (Title of Invention: QWERTY-Type Text Input Interface Device Using Steady State Visual Evoked Potential and Text Input Method) describes a text input interface device, which includes a text display that displays a multiple number of texts in a QWERTY style, an EEG signal measuring unit that measures an EEG signal of a user during the time when a steady state visual evoked potential is evoked by a visual flickering stimulus resulting from the displayed texts, an EEG analyzing unit that analyzes the measured EEG signal, and a text outputting unit that outputs texts corresponding to the analyzed EEG signal.

However, the above conventional text input interface device inevitably induces eye-movement depending on where a user puts his/her attention. In other words, this technique can be conveniently replaced by an eye-tracker device, which can yield further higher accuracy than EEG signals. This is because a user of this technique must overtly move his/her eye focus onto a corresponding keystroke of a keyboard, so as to acquire EEG components for the corresponding letter. Accordingly, the conventional text input interface device has such limitations since it cannot provide correct information (i.e., a user's intention) if a user covertly imagines a certain type of letters without moving his/her eyes.

SUMMARY

In view of the foregoing, example embodiments provide a brain-machine interface apparatus and method for acquiring intention of a user by using an EEG signal generated by a visual stimulus.

However, the problems sought to be solved by the present disclosure are not limited to the above description, and other problems can be clearly understood by those skilled in the art from the following description.

In accordance with an example embodiment, there is provided a brain-machine interface apparatus. The brain-machine interface apparatus may include a display where a plurality of light-emitting points (or lines) flickering with their predefined individual frequencies are arranged; a flickering controller that assigns the plurality of the light-emitting points (or lines) to a plurality of groups, and sets the corresponding individual frequencies for the groups; an EEG measurement unit that measures an EEG signal of a user to be measured who watches the display; a frequency decoder that detects one or more frequency components from the EEG signal; a shape analysis unit that embodies an original shape according to imagination of the target person to be measured based on the one or more detected frequency EEG components and the set frequencies; and a result output unit that outputs information of the embodied original shape.

In accordance with another example embodiment, there is provided a brain-machine interface method through a brain-machine interface apparatus. The brain-machine interface apparatus may include a display where a plurality of light-emitting points (or lines) flickering with their individual frequencies. The brain-machine interface method may include dividing the plurality of the light-emitting points (or lines) into a plurality of groups; controlling the groups to flicker with the different set frequencies; measuring an EEG signal of an individual to be measured who watches the display; detecting one or more frequency components from the measured EEG signal; embodying an original shape according to imagination of the individual (user or subject) to be measured based on the one or more detected EEG frequency components and the set individual frequencies; and outputting information of the embodied original shape.

In accordance with the example embodiments, by using frequency information reflected in an EEG signal measured from a user who watches a flickering stimulus, it is possible to conveniently and exactly reconstruct a shape imagined by the user's EEG signals (particularly, EEG spectral components) to be measured.

In accordance with the example embodiments, since it is possible to variously adjust arrangement and device features of light-emitting devices to be watched by an user, whose EEG signals are measured while watching flickering visual stimuli with a multiple number of individually assigned frequencies, it is possible to accurately estimate a target shape imagined by the user, and furthermore, it is convenient that the device of the present disclosure can be mounted in or cooperated with various types of equipment.

In accordance with the example embodiments, by making light-emitting devices flicker with high frequencies, it is possible to effectively estimate a shape imagined by its user, while alleviating the user's eyestrain.

In accordance with the example embodiments, by integrally outputting a multiple number of shapes through a line arrangement consisting of a multiple number of lines flickering with different frequencies; it is possible to easily provide a visual stimulus for inducing an EEG signal according to its users' imagination.

In accordance with the example embodiments, it is possible to exactly and conveniently restore a shape imagined by a user, by classifying a shape corresponding to a newly measured EEG signal through a classifier produced by means of machine learning technique of pre-labeled training EEG signals.

In accordance with the example embodiments, it is possible to suggest various reference shapes even within a small display by suggesting a visual stimulus through a grid-pattern line arrangement. That is, since miniaturization of the brain-machine interface apparatus is possible, it is easy and convenient that the device can be mounted in or cooperated with various types of equipment.

BRIEF DESCRIPTION OF THE DRAWINGS

FIG. 7 depicts a process of analyzing and restoring a shape imagined by a user, by using an EEG signal through the brain-machine interface apparatus in accordance with another example embodiment.

FIG. 8 is a flow diagram for describing a brain-machine interface method in accordance with another example embodiment.

MODE FOR CARRYING OUT THE INVENTION

Figure 1:
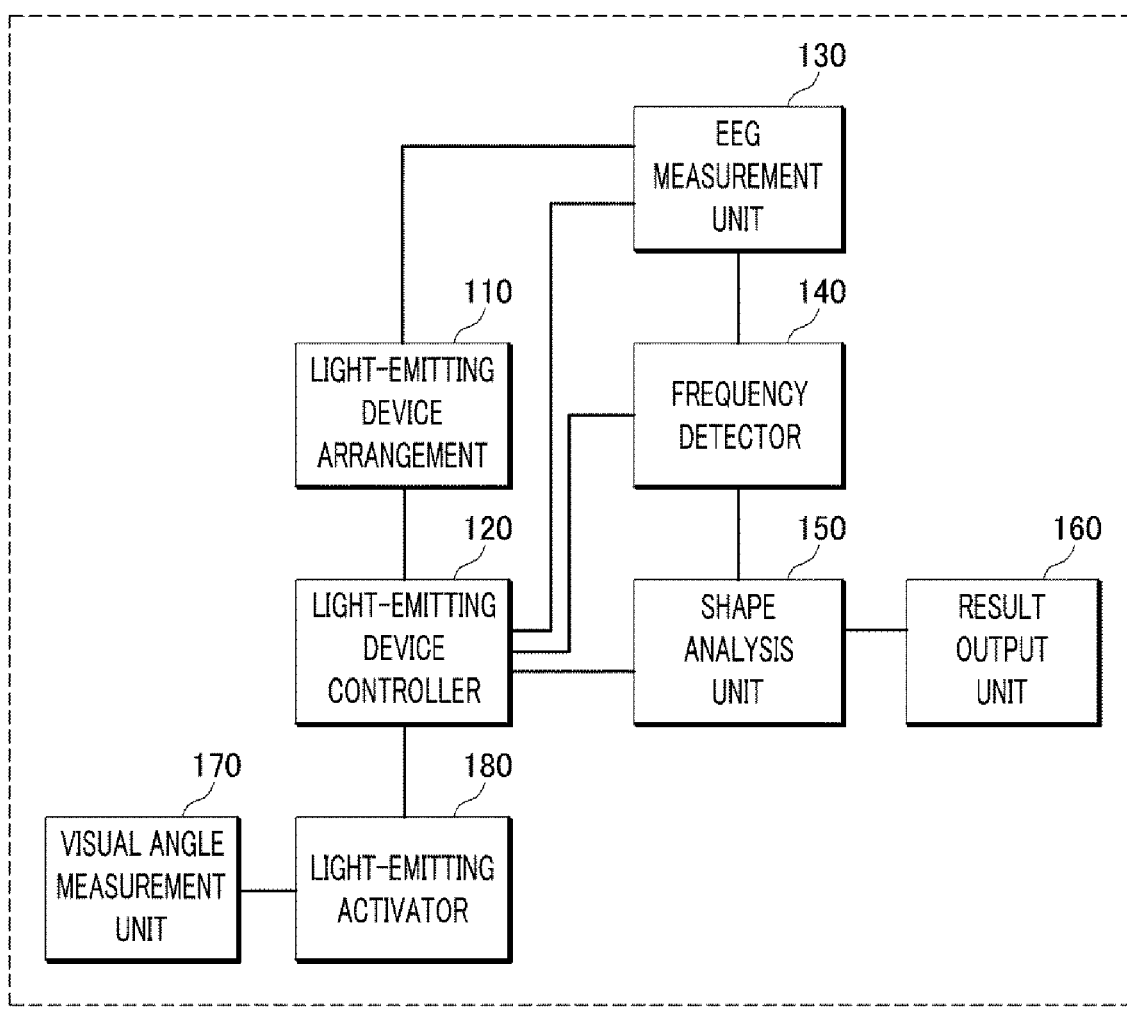
FIG. 1 is a block diagram showing configuration of a brain-machine interface apparatus in accordance with an example embodiment.

Hereinafter, example embodiments will be described in detail with reference to the accompanying drawings so that inventive concept may be readily implemented by those skilled in the art. However, it is to be noted that the present disclosure is not limited to the example embodiments but can be realized in various other ways. In the drawings, certain parts not directly relevant to the description are omitted to enhance the clarity of the drawings, and like reference numerals denote like parts throughout the whole document.

Throughout the whole document, the terms "connected to" or "coupled to" are used to designate a connection or coupling of one element to another element and include both a case where an element is "directly connected or coupled to" another element and a case where an element is "electronically connected or coupled to" another element via still another element. In addition, the term "comprises or includes" and/or "comprising or including" used in the document means that one or more other components, steps, operation and/or existence or addition of devices are not excluded in addition to the described components, steps, operation and/or devices unless context dictates otherwise.

FIG. 1 is a block diagram showing configuration of a brain-machine interface apparatus in accordance with an example embodiment.

As illustrated in FIG. 1, a brain-machine interface apparatus 100 in accordance with an example embodiment includes a light-emitting device arrangement 110, a light-emitting device controller 120, an EEG measurement unit 130, a frequency detector 140, a shape analysis unit 150, a result output unit 160, a visual angle measurement unit 170 and a light-emitting device activator 180.

The light-emitting device arrangement 110 is a display, in which a multiple number of light-emitting points flickering with their individual set frequencies are arranged.

Specifically, the light-emitting device arrangement 110 includes a multiple number of light-emitting devices, which are arranged being spaced from one another. The spacing among the light-emitting devices has a psychophysical meaning, and may be set based on outcomes obtained through pre-experiments. That is, the light-emitting devices are arranged while having sufficient visual discrimination resolution. For example, the spacing may be set such that a maximum length of entire light-emitting device arrangement is formed to the extent that a visual angle is 8 to 10 degrees or less. This is intended to avoid that an image falls on the blind spot of the retina of the eyes, and to enable light of all light-emitting devices to be entirely detected in the photoreceptors on the retina. For example, if five light-emitting devices are arranged in each of rows and columns, and spacing between light-emitting devices is 1 cm, a length of each of the rows and the columns becomes 5 cm, and a diagonal length formed by this arrangement becomes $5\sqrt{2}$ cm. Accordingly, when the light-emitting device arrangement is watched in a distance of 1 m, a visual angle becomes $2 \times \arctan(0.05 \times \sqrt{2}/2)$. This visual angle corresponds to a size of about 4 degrees. As a result, all light-emitting visual stimuli do not reach the blind spot of the retina of a subject, and fall on the center of the fovea area where visual information processing occurs the most precisely. Therefore, this technology does not necessarily demand gaze-shift (i.e., macroscopic eye-movement), which is advantageous as compared to the conventional similar devices. That is, only covert attentional shift is necessary to use this technology without obvious eye-movement. For example, the above-described arrangement of rows and columns may be an example for preferable light-emitting device arrangement.

The light-emitting devices may be light emitting diodes (LEDs), and either red or green light emitting diodes. This is because photoreceptor cone cells for red and green colors are dominantly distributed in the fovea of the human being's retina. For reference, white diodes may be adopted to use the rod cells widely distributed in the most peripheral part of the retina. In addition, under the condition of luminance of light emitting diodes, red or white light emitting diodes, which have relatively high luminance, may be used as the light-emitting devices.

Meanwhile, as illustrated in FIG. 2A, FIG. 2B, FIG. 3A and FIG. 3B, in the light-emitting device arrangement 110, a multiple number of light-emitting devices may be arranged in a matrix form. In this case, the light-emitting devices are arranged being spaced from one another with a certain interval, and two or more light-emitting devices may be arranged at each position where a row and a column cross with each other. Accordingly, a single row and a single column do not share one light-emitting device at their crossing position, and each of the row and the column independently has a light-emitting device. This is intended to enable each of rows and columns to flicker with its unique independent frequency.

Figure 2A:
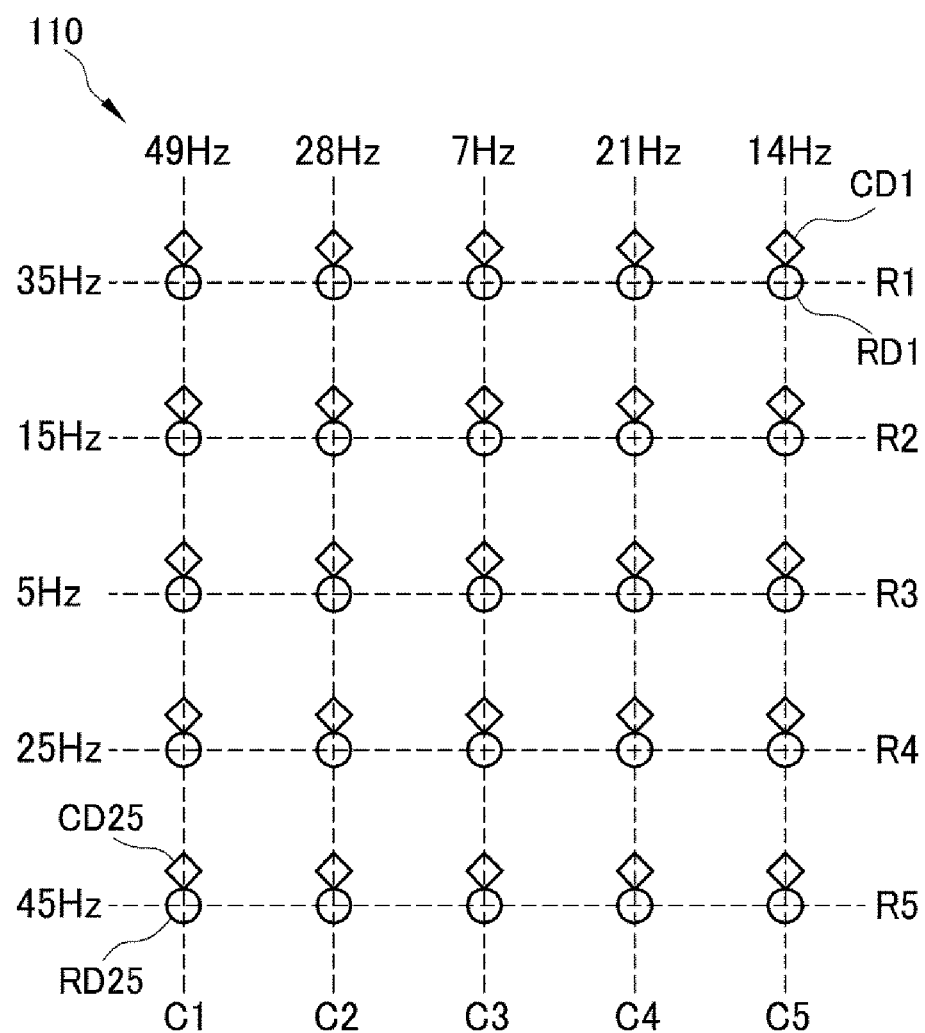
FIG. 2A depicts an arrangement method of light-emitting devices in accordance with an example embodiment.
Figure 2B:
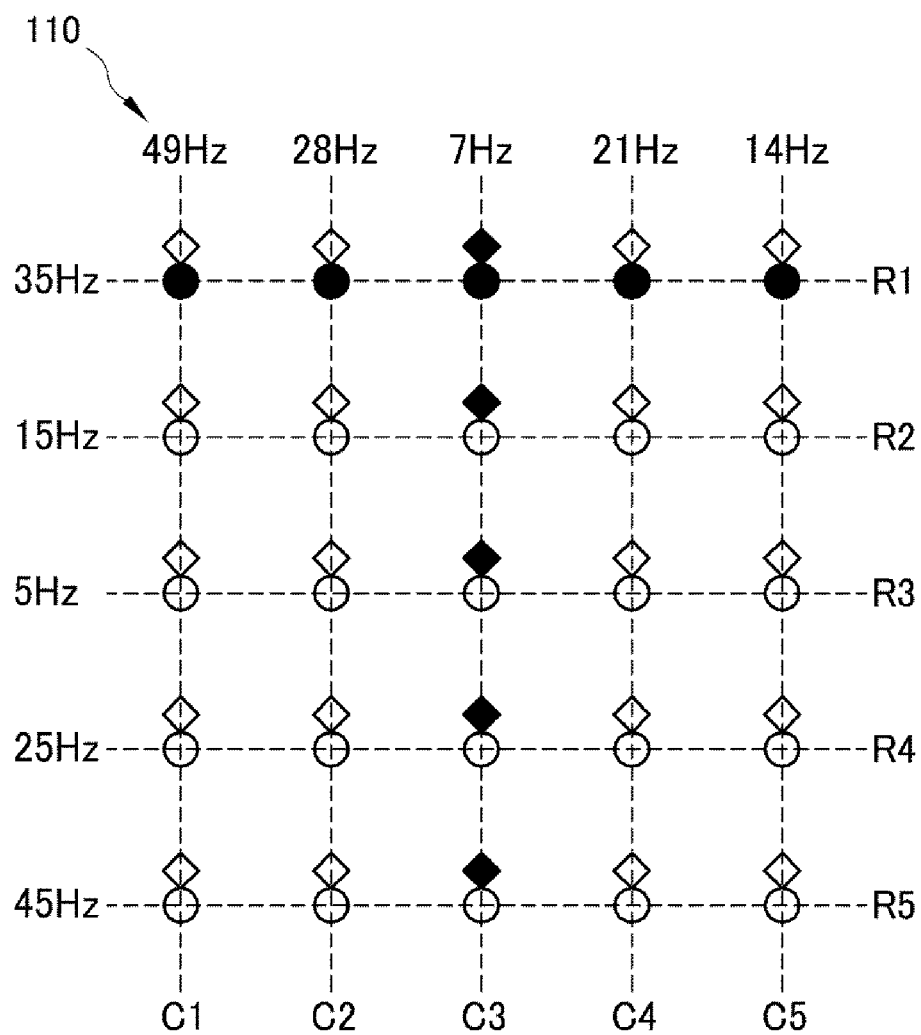
FIG. 2B depicts a method of estimating an imagined shape ('T' shape) by using the arrangement method of light-emitting devices in accordance with an example embodiment.
Figure 3A:
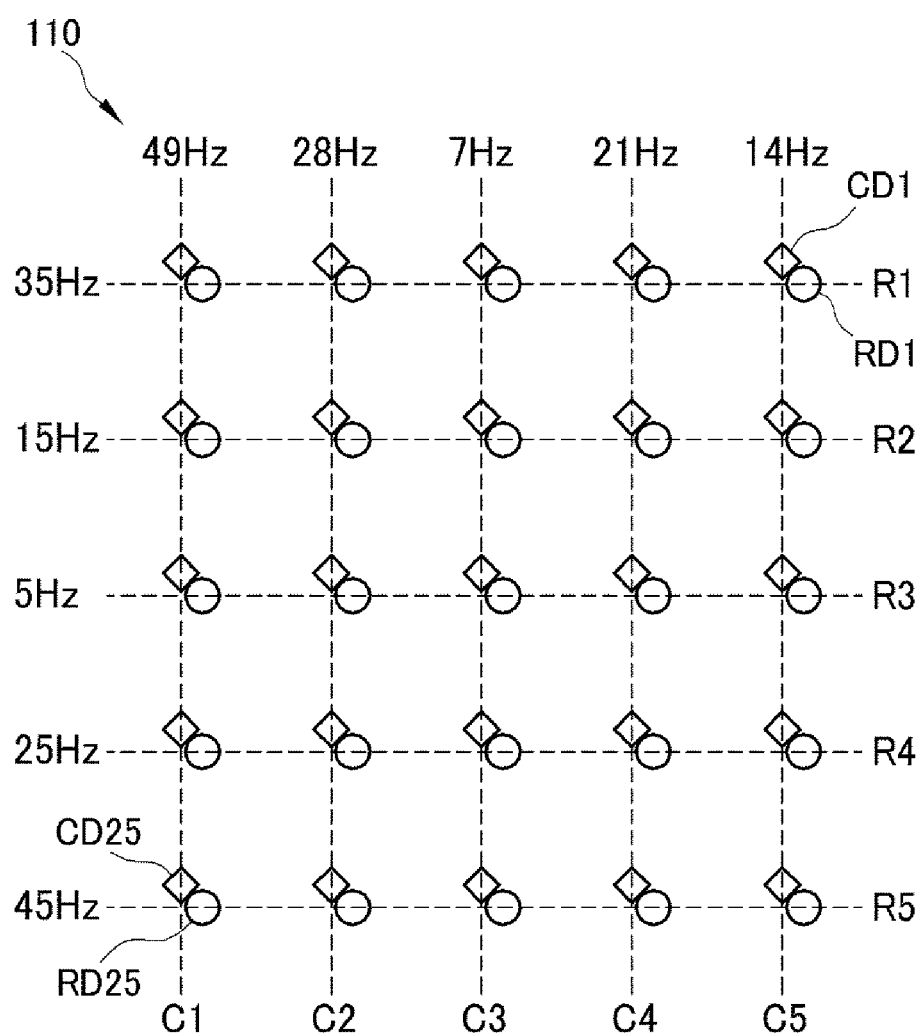
FIG. 3A depicts an arrangement method of light-emitting devices in accordance with another example embodiment.
Figure 3B:
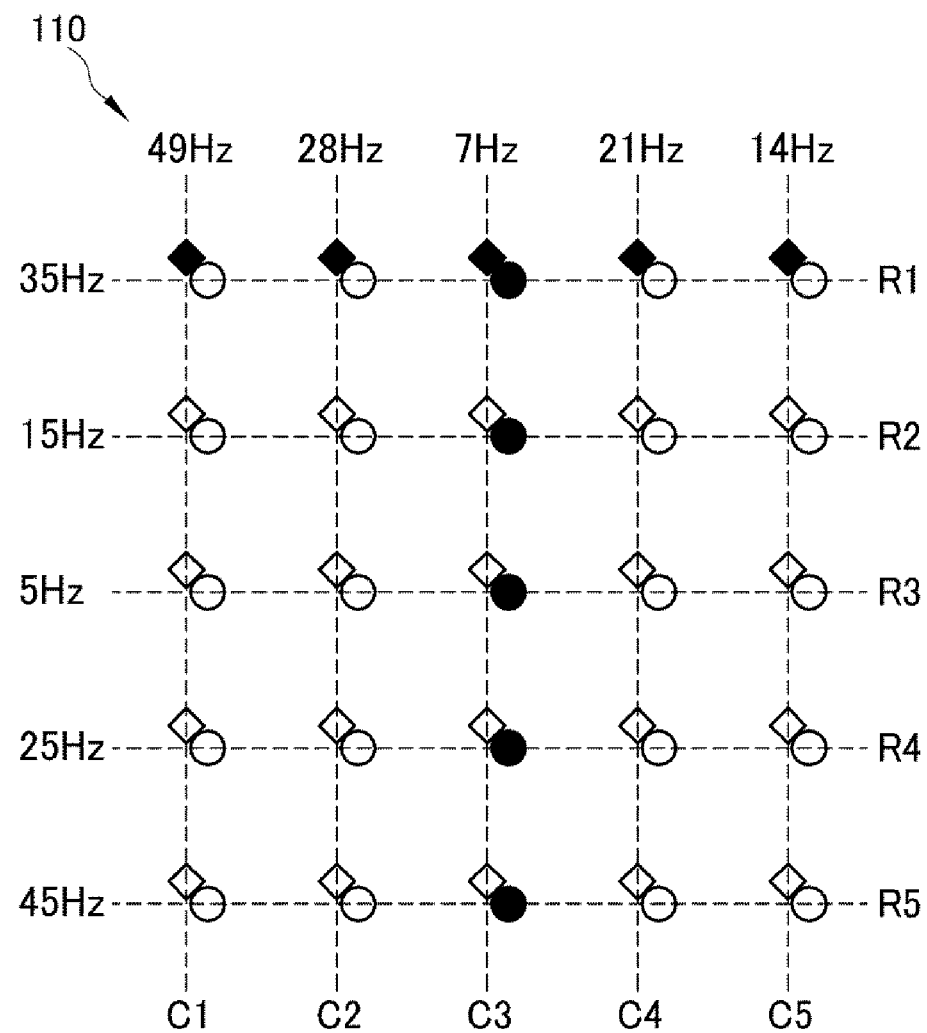
FIG. 3B depicts a method of estimating an imagined shape ('T' shape) by using the arrangement method of light-emitting devices in accordance with another example embodiments.

FIG. 2A and FIG. 2B depict an arrangement method of light-emitting devices and a method for estimating an imagined shape by using the arrangement method in accordance with an example embodiment. FIG. 3A and FIG. 3B depict an arrangement method of light-emitting devices and a method for estimating an imagined shape by using the arrangement method in accordance with another example embodiment (diagonal configuration).

In the light-emitting device arrangement of FIG. 2A, FIG. 2B, FIG. 3A and FIG. 3B, marks (RD1 to RD25) for light-emitting devices of rows (R1 to R5) are different from those (CD1 to CD25) for light-emitting devices of columns (C1 to C5); however, this marking is intended to facilitate discrimination of rows and columns, and light-emitting devices of rows and columns may be the same in type.

Specifically, FIG. 2A, FIG. 2B, FIG. 3A and FIG. 3B show five rows and five columns of the light-emitting device arrangement 110. That is, a single row has five light-emitting devices (RD1 to RD25), and a single column has five light-emitting devices (CD1 to CD25). For reference, a size of the light-emitting device matrix of the light-emitting device arrangement 110 may be variously set.

For example, FIG. 2A and FIG. 2B illustrate that the light-emitting devices of the light-emitting device arrangement 110 are arranged in line at the cross points of the matrix.

In another example, FIG. 3A and FIG. 3B illustrate that the light-emitting devices of the light-emitting device arrangement 110 are diagonally arranged at the cross points of the matrix. In this case, it is possible to make the arrangement of all the light-emitting devices closer to the square shape, than that when the light-emitting devices are arranged in line at cross points as in FIG. 2A and FIG. 2B. This is intended to enable its user to more easily watch the light-emitting device arrangement 110, and to enable a shape of a signal or letter, which will be embodied by the light-emitting device arrangement 110, to be symmetric and conform to a real shape.

Returning to FIG. 1, the light-emitting device controller 120 divides a multiple number of light-emitting points into a multiple number of groups, and sets individually different set frequencies for the groups. That is, the light-emitting device controller 120 controls a multiple number of light-emitting points to flicker with different set frequencies by groups of the light-emitting points.

Specifically, the light-emitting device controller 120 divides the light-emitting devices of the light-emitting device arrangement 110 into a multiple number of groups (i.e., conception or imagination unit), and controls the light-emitting devices to flicker with the different set frequencies for the groups. For reference, the light-emitting device controller 120 may set the light-emitting devices that a user will watch, to flicker with high frequencies, and thereby, alleviating the user's eyestrain.

For example, the light-emitting device controller 120 may group the multiple light-emitting devices according to a multiple number of preset arrangement position ranges. That is, the light-emitting device controller 120 may divide a multiple number of light-emitting devices arranged in one row or column, among the overall light-emitting devices, into one group.

In addition, the light-emitting device controller 120 may set different set frequencies for the multiple groups, and control light-emitting devices belonging to each of the groups to flicker with an identical set frequency. For example, as shown in FIG. 2A, FIG. 2B, FIG. 3A and FIG. 3B, 35 Hz, 15 Hz, 5 Hz, 25 Hz and 45 Hz may be set for the five rows of the light-emitting device arrangement 110, respectively, and 49 Hz, 28 Hz, 7 Hz, 21 Hz and 14 Hz may be set for the five columns thereof, respectively.

The light-emitting device controller 120 may set bandwidths of the set frequencies for neighboring rows or columns on the light-emitting device arrangement 110 to be broad. The light-emitting device controller 120 may set a difference in bandwidth between the frequencies for the rows or the columns to be a reference value or more. This is intended to improve resolution and reliability of a measurement value to be obtained upon detection of frequencies on a user's EEG signal detected through the EEG measurement unit 130, which will be described later.

In addition, the light-emitting device controller 120 may assign set frequency to the respective rows and columns, to make a sum of frequencies according to combination (or its harmonic frequencies) of one row and one column on the light-emitting device arrangement different from a sum of frequencies (or harmonic frequencies) according to combination of another row and another column. This is because it makes easier to decode the detected or different-frequency combined EEG frequency components (i.e. steady state visual evoked potentials (SSVEPs)) into the assigned frequency combination between a specific row and a specific column.

For example, in the state that the light-emitting devices arranged as shown in FIG. 2A and FIG. 3A are flickering with different frequencies, a user may watch the light-emitting device arrangement 110, with imagining the letter "T". In this case, as shown in FIG. 2B or 3B, frequencies of SSVEP expected to be detected are 7 Hz (i.e., column C3), 35 Hz (i.e., row R1) and 42 Hz, which is a sum of the two frequencies. In another example, if a user watches the light-emitting device arrangement in the flickering state, imagining the letter "+", frequencies of SSVEP expected to be detected are 7 Hz (row C3), 5 Hz (row R3), and 12 Hz, which is a sum of the two frequencies.

As described above, set frequencies may be set for each individual row and column of the light-emitting devices, such that sums (i.e., 42 Hz and 12 Hz as in the above examples) of frequencies according to combinations of rows and columns, which correspond to different shapes, are different from each other.

Specifically, in case of the light-emitting device arrangement illustrated in FIG. 2A, FIG. 2B, FIG. 3A and FIG. 3B, the number of all combinations, which can be accomplished by the five rows and the five columns, is 25. That is, the number of frequency sums by combinations of rows and columns is 25. In this case, frequencies are assigned to the overall rows and columns on the light-emitting device arrangement, such that the 25 frequency sums are different from one another. Meanwhile, FIG. 1 has described that the brain-machine interface apparatus 100 in accordance with an example embodiment includes the light-emitting device arrangement 110 and the light-emitting device controller 120 as separate components. However, in another example, the light-emitting device arrangement 110 and the light-emitting device controller 120 may be combined with each other to be a single component. In this case, the component according to the combination of the light-emitting device arrangement 110 and the light-emitting device controller 120 may be connected to the EEG measurement unit 130, the frequency detector 140, and the shape analysis unit 150, which will be described later, to provide frequency information set for each of the light-emitting devices and control information of the light-emitting devices (e.g., information of onset and offset of flickering control).

The EEG measurement unit 130 measures an EEG signal of a user who watches a display. Specifically, the EEG measurement unit 130 measures an EEG signal of a user who watches the light-emitting devices of the light-emitting device arrangement 110, and transfers the measured EEG signal to the frequency detector 140.

The EEG measurement unit 130 may measure an EEG signal in various manners, and especially, measure a steady state visual evoked potential (SSVEP) physically induced from the external flickering visual stimuli, detected around the visual cortex of the occipital lobe.

For reference, the EEG measurement unit 130 may be connected to EEG measurement equipment (not illustrated) to control the equipment to an EEG signal. In addition, in accordance with another example embodiment, at least one component including the EEG measurement unit 130 among the components of the brain-machine interface apparatus 100 may be included as one component within the EEG measurement equipment. For example, EEG measurement equipment in a headset form may be applied for convenience of its user.

The frequency detector 140 detects at least one frequency or a combined (or harmonic) frequency of a multiple number of frequencies from the received EEG signals.

Specifically, when a user imagines his/her intended specific shape in the state of watching the light-emitting device arrangement 110, his/her attention is selectively focused to a light-emitting device arrangement matched with the shape imagined by the user on the light-emitting device arrangement 110. Accordingly, the same frequencies as frequencies of light-emitting devices belonging to the light-emitting device arrangement, to which the user's attention is focused, are reflected in an EEG signal. That is, an EEG signal reflecting cognitive intention of the user who is watching the light-emitting device arrangement unit 110 is detected.

In this case, with respect to the frequencies of the EEG signal that have been detected through the frequency detector 140, frequencies of groups corresponding to the shape imagined by the user, and a sum (or their harmonics) of the frequencies of the corresponding groups are detected. If the frequency components of the detected EEG signal include frequencies consistent with the frequencies set through the light-emitting device controller 120, harmonic frequencies of the consistent frequencies, and similar frequencies of the periphery of the corresponding frequencies, the frequency detector 140 may determine accurate frequencies matched with the shape imagined by the user, with reference to frequencies related to the shape that can be imagined by the user among the frequencies set through the light-emitting controller 120, and a sum of the frequencies.

The shape analysis unit 150 embodies an original shape according to the imagination of the user, based on one or more frequency components detected from the EEG signals measured from the user, and the set frequencies for the multiple light-emitting device groups.

Specifically, the shape analysis unit 150 detects light-emitting device groups, which correspond to the frequencies detected by the frequency detector 140 among the multiple groups on the light-emitting device arrangement 110, and a combined frequency thereof. In addition, the shape analysis unit 150 restores a shape based on the arrangement form of the detected light-emitting device groups, and estimates an original shape imagined by the user based on the decoded shape.

In this case, if two or more frequencies are detected through the frequency detector 140, the shape analysis unit 150 may estimate the imagined shape by combining arrangement forms of light-emitting devices by the groups of the light-emitting device arrangement 110, which correspond to the two or more detected frequencies.

For example, with reference to FIG. 2B and FIG. 3B, a method for estimating a shape imagined by an individual using the light-emitting device arrangement 110 is described.

If a subject imagines the letter "T" as shown in FIG. 2B and FIG. 3B, the frequency detector 140 detects, from the subject's EEG signals, the frequencies of 35 Hz and 7 Hz, which correspond to the shape of the letter "T", among the groups (i.e., rows and columns) on the light-emitting device arrangement 110. Also, the frequency detector 140 may detect 42 Hz, which is a sum of 35 Hz and 7 Hz.

The shape analysis unit 150 determines groups (i.e., rows and columns) on the light-emitting device arrangement 110, which correspond to 35 Hz, 7 Hz and the combined frequency of 42 Hz that have been detected through the frequency detector 140, and determines the shape (i.e., the shape corresponding to the letter "T") based on the arrangement form of the light-emitting devices corresponding to the determined groups.

Meanwhile, the shape analysis unit 150 calculates similarity between multiple pre-stored reference shapes and the shape according to the arrangement form of the light-emitting devices of the detected groups. The shape analysis unit 150 may estimate a reference shape having the highest similarity to be the shape imagined by the subject. The shape analysis unit 150 may pre-store reference shapes, which include various types of shapes such as letters, numerals and symbols, matching them with information of the light-emitting device groups, which correspond to the reference shapes, on the light-emitting device arrangement 110.

Returning to FIG. 1, the result output unit 160 outputs shape information for the original shape embodied by the shape analysis unit 150. The result output unit 160 may output the shape information as display information that can be identified, such that a user (e.g., a subject to be measured) can discriminate the information with the user's naked eyes or through listening, or transfer the corresponding information to a preset related device.

That is, the result output unit 160 may output the information of the original shape as display information including at least one of a discriminable shape, letter, numeral and symbol. For example, when the estimation of the original shape using the user's EEG signals is completed, the result output unit 160 may output the shape imagined by the user on the light-emitting device arrangement 110.

Meanwhile, the brain-machine interface apparatus 100 in accordance with an example embodiment may output a signal including the information of the original shape to a preset cooperative related device. For example, the brain-machine interface apparatus 100 may be equipped in a remote control of a home appliance like a TV. In this case, if a user watches the small light-emitting device arrangement equipped in the remote control in the state of imagining his/her intended letter, numeral, symbol, etc., the brain-machine interface apparatus 100 may perform preset operations through analysis of the EEG of the user. For example, if a user imagines the letters 'A,' 'B,' and 'C' in this order in the state of watching the remote control equipped with the small light-emitting device arrangement 110, the brain-machine interface apparatus 100 may estimate and determine the letters "ABC" through the EEG analysis. In addition, in order to enable a TV channel in response to the letter information of the determined "ABC" to be automatically selected, the result output unit 160 may transmit the corresponding information to a preset related device (i.e., a receiving device of a TV).

In addition, as the brain-machine interface apparatus 100 may be equipped in a certain device like a smart phone or others, even if a user only imagines various shapes, it is possible to transfer the corresponding shapes to a certain related device or software.

Meanwhile, the brain-machine interface apparatus 100 in accordance with an example embodiment may enable a user to conduct imagination according to one's intention in the state of watching the light-emitting device arrangement 110 without moving his/her eyes (i.e., no gaze-shift), and accordingly, enable the imagined shape to be estimated and the result to be output.

Specifically, as illustrated in FIG. 1, the brain-machine interface apparatus 100 in accordance with an example embodiment may further include a visual angle measurement unit 170 and a light-emitting device activator 180.

The visual angle measurement unit 170 measures a maximum visual angle and an effective visual angle at a distance of preset spacing from the light-emitting device arrangement 110 when focus of a user toward the light-emitting device arrangement 110 is maintained. For reference, the maximum visual angle may be set to be a viewing angle, at which a target person to be measured can view without moving his/her eyes, and the effective visual angle may be set to be a viewing angle, at which a target person to be measured can relatively accurately (i.e., effectively) identify information within the maximum visual angle.

For example, the brain-machine interface apparatus 100 may further include a separate member (not illustrated) to measure a visual field of a user at a certain area of the forepart of the light-emitting device arrangement 110, and the visual angle measurement unit 170 may receive a visual field measurement value from the member (not illustrated) for the visual field measurement so as to calculate the maximum visual angle and the effective visual angle.

The light-emitting device activator 180 selects light-emitting devices to be activated from the multiple light-emitting devices on the light-emitting device arrangement 110 based on at least one of the maximum visual angle and the effective visual angle that have been measured.

Specifically, the light-emitting device activator 180 selects a range of light-emitting devices arranged within the measured maximum visual angle based on the focus of the target person to be measured, and activates only the light-emitting devices within the selected range.

In this case, the light-emitting device controller 120 may divide the light-emitting devices selected by the light-emitting device activator 180 into a multiple number of groups and control the groups to flicker with different frequencies.

Meanwhile, the brain-machine interface apparatus 100 in accordance with another example embodiment may embody the light-emitting device arrangement 110 itself to secure a user's visual angle. Specifically, through a prior experiment or the like, a physical size of the light-emitting device arrangement unit 110, spacing among the light-emitting devices, and others may be set such that a visual angle of a target person to be measured is fixed within a preset distance from the light-emitting device arrangement 110.

Hereinafter, a brain-machine interface method in accordance with an example embodiment is described in detail with reference to FIG. 4.

Figure 4:
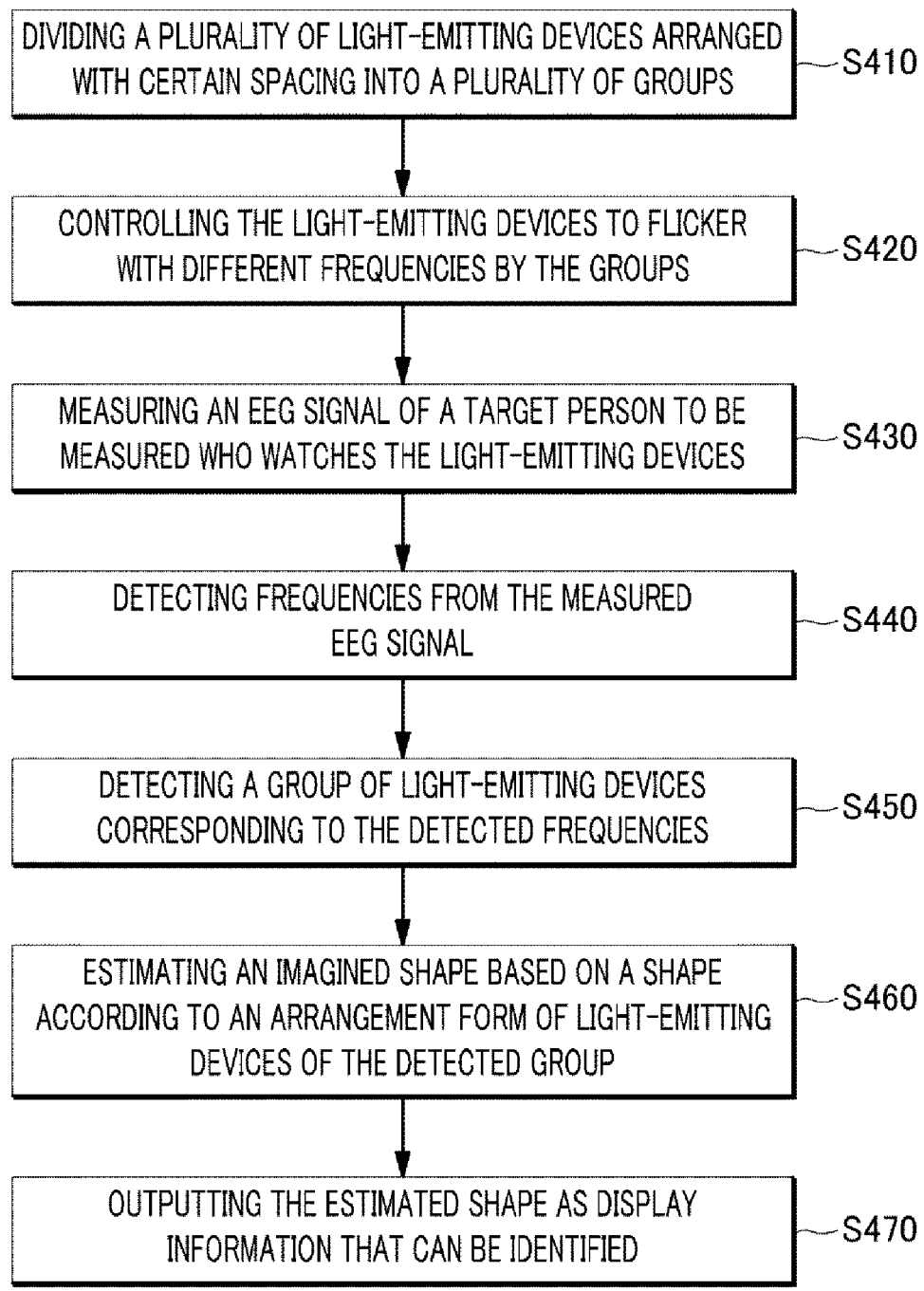
FIG. 4 is a flow diagram for describing a brain-machine interface method in accordance with an example embodiment.

FIG. 4 is a flow diagram for describing a brain-machine interface method in accordance with an example embodiment.

First, the multiple light-emitting devices, which are arranged with a certain interval, are divided into a multiple number of groups (S410).

In this case, the multiple light-emitting devices may be divided into a multiple number of groups based on a multiple number of arrangement position ranges. For example, the multiple light-emitting devices may be arranged in a matrix form, in which two or more light-emitting devices are arranged at each position where a single row and a single column cross with each other, and each of the rows and columns may be set to one group.

Thereafter, different frequencies are set for the groups to control light-emitting devices within the groups to flicker with their respective set frequencies (S420).

As described above, the two or more light-emitting devices positioned at a cross point of a row and a column on the light-emitting device matrix are controlled to flicker with frequencies of different groups. For reference, a bandwidth difference between frequencies of neighboring rows or columns may be set to be a preset reference value or more. In addition, a frequency sum according to combination of one row and one column may be set to be different from a frequency sum according to combination of another row and another column.

Thereafter, in the state that the multiple light-emitting devices are flickering, an EEG signal of a user who watches the light-emitting devices is measured (S430).

In this case, the subject, whose EEGs are measured, intends and imagines a specific shape (i.e., a specific letter, numeral, symbol and others) while watching the multiple light-emitting devices. Accordingly, their corresponding steady state visual evoked potentials (SSVEPs) may be detected around the subject's occipital lobe.

Thereafter, at least one frequency and a combined (or harmonic) frequency of related frequencies are detected from the measured EEG signals (S440).

In this case, the detected frequencies are associated with flickering frequencies of light-emitting device groups corresponding to a geometry or shape intended by the user.

Specifically, after S420, if the user imagines a specific shape in the state that he/she watches the flickering light-emitting devices, the same frequencies as those of the light-emitting devices arranged at positions corresponding to the specific shape are detected from his/her EEG signals.

Next, a group of light-emitting devices corresponding to the detected frequencies are detected (S450).

That is, among the multiple groups, groups set with the frequencies corresponding to the frequencies detected from the EEG signals of the subject are detected.

Thereafter, the shape imagined by the subject is estimated based on a shape according to an arrangement form of light-emitting devices of the detected groups (S460).

In this case, if two or more groups are detected, the shape imagined by the subject may be estimated by combining shapes according to arrangement forms of light-emitting devices of the detected groups. It is also possible to calculate similarity between pre-stored multiple reference shapes and the shapes according to the detected groups, and estimate a shape having the highest similarity as the shape imagined by the target person to be measured.

Thereafter, the estimated shape is output as display information that can be identified (S470).

In this case, in an example embodiment, it is also possible to transmit the information of the estimated shape to a preset related device in S470.

Meanwhile, the brain-machine interface method in accordance with an example embodiment may first perform the step of measuring a maximum visual angle and an effective visual angle at a distance of preset spacing from the light-emitting devices when a user's focus toward the light-emitting devices is maintained, and the step of selecting light-emitting devices to be activated among the multiple light-emitting devices based on the measured maximum visual angle and effective visual angle, prior to S410. That is, in S410, the selected light-emitting devices may be divided into a multiple number of groups, and the follow-up sets may be performed.

As a result, the subject can continuously imagine various shapes in the state that the subject fixes his/her eyes without moving the eyes, and the shapes imagined by the subject can be accurately estimated and provided.

Hereinafter, a brain-machine interface apparatus and a method thereof in accordance with another example embodiment are described in detail with reference to FIG. 5 to FIG. 8.

Figure 5:
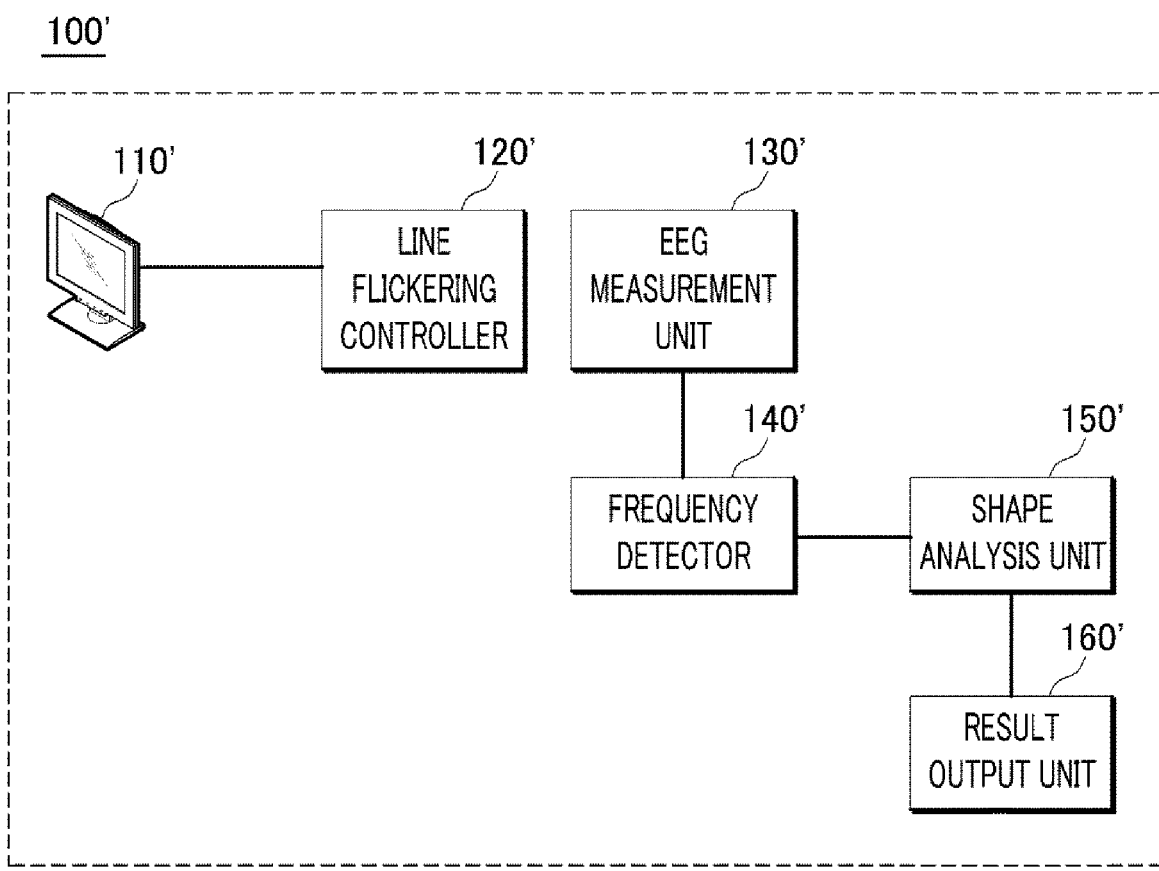
FIG. 5 shows configuration of a brain-machine interface apparatus in accordance with another example embodiment.
Figure 6A:
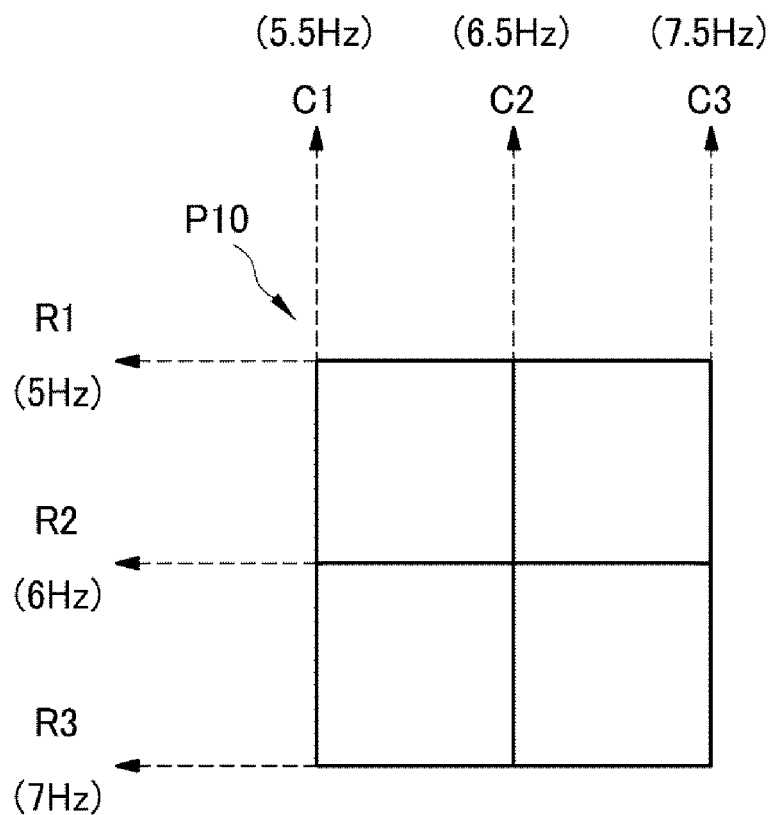
FIG. 6A shows an example for a line arrangement for a visual stimulus in accordance with another example embodiment.
Figure 6B:
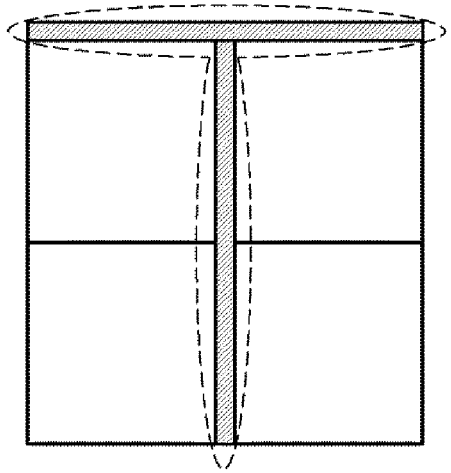
FIG. 6B shows an example for a shape (e.g. 'T' shape), which corresponds to a user's imagination, on the line arrangement for a visual stimulus in accordance with another example embodiment.

FIG. 5 is a block diagram showing configuration of a brain-machine interface apparatus in accordance with another example embodiment. FIG. 6A shows an example for line arrangement as a grid-shaped visual flickering stimuli in accordance with another example embodiment, and FIG. 6B shows an example for a shape (e.g., 'T'), which corresponds to a user's imagination, on the line arrangement as a grid-shaped visual flickering stimuli.

First, as illustrated in FIG. 5, the brain-machine interface apparatus 100' in accordance with another example embodiment includes a display 110', a line flickering controller 120', an EEG measurement unit 130', a frequency detector 140', a shape analysis unit 150' and a result output unit 160'.

The display 110' outputs an arrangement of a multiple number of light emitting points flickering with their respective set frequencies.

Specifically, the display 110' outputs, to a screen (or a monitor or a display), a line arrangement consisting of light flickering lines, in which a certain number of light-emitting points are continuously formed in each of the lines. For example, the display 110' includes any devices or means capable of outputting light-emitting lines on a screen, regardless of materials and sizes, such as a liquid crystal display (LCD) and a light emitting diode (LED).

Line arrangement may be fully arranged on the entire screen of the display 110', or a certain size of line arrangement may be output on a black background screen. In this case, the screen size of the display 110' or the size of the line arrangement to be output on the screen may be designed to be enough to not require macroscopic eye-movement (i.e., no obvious gaze-shift) of a user who watches the display 110'. Further, with respect to a position where the display 110' is installed, the display 110' may be positioned in a proper distance enough to not require macroscopic eye-movement of the user.

The display 110' outputs the line arrangement where light-emitting lines are arranged with a certain space (FIG. 6A), on the screen. In this case, the spacing of the light-emitting lines has a psychophysical meaning, and may be set based on outcomes obtained through pre-experiments. That is, the light-emitting lines are arranged to have sufficient visual discrimination resolution. For example, the spacing of the light-emitting lines may be set such that a visual angle by a maximum size (or length) of the line arrangement is 8° to 10° or less. This is intended to avoid that an image on the retina of the eyes falls on the blind spot, and to enable light of all the light-emitting lines to be entirely and securely detected by the photoreceptors in the retina. That is, a visual stimulus by the line arrangement does not reach the blind spot of the subject's retina, and falls on the center of the fovea where the most accurate visual information processing occurs.

In addition, the compact line arrangement is intended to induce electroencephalographic (EEG) signals (particularly, steady state visual evoked potentials (SSVEPs)) of the subject by an externally flickering visual stimulus. Accordingly, the display 110' outputs a line arrangement, in which each of the light-emitting lines has certain luminance (e.g., average luminance of 536 cd/m$^2$). In this case, each of the light-emitting lines may be displayed in any one of red or green color. This is because the photoreceptor cone cells detecting red or green colors are dominantly distributed in the fovea of the human being's retina. In addition, each of the lines of the line arrangement may be displayed in white or gray, in order to use the rod cells widely distributed in the most peripheral part of the retina. Besides, each of the light-emitting lines may be displayed in any color that can be visually recognized.

For example, as illustrated in FIG. 6A and FIG. 6B, in a line arrangement in accordance with another example embodiment, two or more light-emitting lines may be arranged in a grid shape.

As shown in FIG. 6A, a line arrangement P10 may be in a matrix form. For example, FIG. 6A and FIG. 6B show that the line arrangement P10 consists of three row lines (R1 to R3) and three column lines (C1 to C3). The line arrangement may include three row lines and three column lines, which flicker with different frequencies and are spaced from one another at a certain interval, and in which a row or column line may cross with one or more row or column line. The grid-shaped line arrangement, which includes three row lines and three column lines, may be embodied in an ultraminiature form and can represent various shapes (e.g., letters, numerals, etc.) so that it can be easily applied to any equipment. However, a form of a line arrangement and the number of light-emitting lines included therein in accordance with another example embodiment are not limited to those described above. For example, as the number of light-emitting lines included in a line arrangement increases, the number of shapes that can be imagined by a user increases, and a more accurate shape can be imagined. That is, the more number of line segments are formed, the further letter-like shape is accomplished.

Returning to FIG. 5, the line flicking controller 120' divides a multiple number of light-emitting lines into a multiple number of groups, and sets different set frequencies for the groups. In this case, the line flickering controller 120' divides each light-emitting line of a line arrangement into one group. In addition, the line flickering controller 120' sets different set frequencies (hereinafter, referred-to as 'flickering frequencies') for the light-emitting lines included in the line arrangement, and controls the light-emitting lines to flicker with the different frequencies.

The line flickering controller 120' may randomly assign the set multiple flickering frequencies to the respective lines of the line arrangement. In this case, the line flickering controller 120' may set effective flickering frequencies (e.g., 5 Hz to 7.5 Hz) to induce a steady state visual evoked potential (SSVEP) of the user's EEG signals.

In addition, the line flickering controller 120' may set a difference of bandwidths of the frequencies by the rows or the columns on the line arrangement to be a reference value or more. This is intended to improve resolution and reliability of a measurement value, which is measured through the EEG measurement unit 130' to be described later upon detection of frequencies from the EEG signal of the target person to be measured.

For example, FIG. 6A shows that in the line arrangement P10, a first row line R1 is set to flicker with 5 Hz, a second row line R2 is set to flicker with 6 Hz, and a third row line R3 is set to flicker with 7 Hz. In addition, in the line arrangement P10, a first column line C1 is set to flicker with 5.5 Hz, a second column line C2 is set to flicker with 6.5 Hz, and a third column line C3 is set to flicker with 7.5 Hz. Like this, different flickering frequencies are set for the lines of the line arrangement P10.

In addition, the line flickering controller 120' continuously keeps and suggests flickering stimuli in all the column and row lines, while maintaining the flickering frequencies designated for the respective lines of the line arrangement P10.

For example, as shown in FIG. 6A, it is assumed that all the light-emitting lines included in the line arrangement are continuously flickering with their respective unique flickering frequencies. In this case, as shown in FIG. 6B, when a user's attention is given to lines corresponding to a specific shape (e.g., "ㅜ" which is a Korean phoneme in FIG. 6B), a leading feature aspect of the user's EEGs corresponds to a component combination of the first row line R1 and the second column line C2. The shape (e.g., 'letters') that can be imagined by the user includes shapes according to any possible combination that can be accomplished in the grid line arrangement. Likewise, when a user's attention is focused to the lines corresponding to the shape "⊥" in the flickering line arrangement, the user's EEG feature corresponds to a component combination of the third row line R3 and the second column line C2 in the line arrangement P10.

In case of the shape "□", a user's EEG feature corresponds to a component combination of the first and third row lines R1 and R3 and the first and third column lines C1 and C3.

For reference, the line flickering controller 120' may set the flickering frequencies for the lines to high frequencies so as to alleviate a user's eyestrain. Also, the line flickering controller 120' may set the luminance of all the lines to be the same in order to exclude any effect resulting from a difference in luminance of the lines.

Returning to FIG. 5, the EEG measurement unit 130' measures an EEG signal of a user who watches the individually flickering line arrangement on the screen of the display 110', to provide the measured EEG signal to the frequency detector 140'. In this case, the EEG measurement unit 130' may measure an EEG signal in various manners, and measure a user's steady state visual evoked potentials (SSVEPs), which are physically driven by externally flickering visual stimuli.

For reference, the EEG measurement unit 130' may be connected to EEG measurement equipment (not illustrated) to control the equipment to measure an EEG signal, and at least one component including the EEG measurement unit 130' among the components of the brain-machine interface apparatus 100' may be included as one component within the EEG measurement equipment. For example, EEG measurement equipment in a headset form may be applied for a user's convenience.

The frequency detector 140' detects at least one frequency from the measured EEG signal. In this case, the frequency detector 140' may detect one or more individual frequencies and a frequency component of a combination (or harmonics) of two or more frequencies.

Specifically, if a user imagines a specific shape (i.e., an original shape) in the state that he/she watches the grid-shaped line arrangement output on the screen of the display 110', individual frequencies of lines matched with the shape imagined by the user and the same frequency as a combined frequency of the individual frequencies are detected from his/her EEG signals. That is, if a user imagines a specific shape in the state that the user watches the line arrangement where lines corresponding to a multiple number of shapes are flickering and output, an EEG signal according to the user's cognitive intention corresponding to a specific shape is decoded.

In this case, the frequency detector 140' may perform feature extraction processing on a user's EEG signal to detect one or more frequencies. The frequency detector 140' may detect a frequency component from an EEG signal through a preset frequency analysis method (e.g., Fast Fourier Transform). The frequencies detected by the frequency detector 140' may include one or more individual frequencies, harmonic frequencies of the individual frequencies, and similar frequencies of the periphery of the individual frequencies. In this case, the frequency detector 140' may detect feature frequencies to be used for shape analysis with reference to flickering frequencies by preset lines and a combination of the flickering frequencies by the lines.

For example, if a subject imagines the shape "ㅜ" while watching the line arrangement P10 as shown in FIG. 6A, a frequency corresponding to a combination of the first row line R1 and the second column line C2 (indicated by a dotted line in FIG. 6B) is detected from the user's EEG signals. That is, the frequency detector 140' may detect at least one frequency of 5 Hz, 6.5 Hz and their combination thereof.

The shape analysis unit 150' embodies an original shape according to a user's imagination based on the one or more frequency components detected through the frequency detector 140' and the set frequencies by the lines. In this case, the shape analysis unit 150' may perform preset pattern recognition processing for the frequencies detected by the frequency detector 140' to classify a shape corresponding to the detected frequencies, and embody the original shape imagined by the subject based on the classification result.

The original shape analysis process through the shape analysis unit 150' is described in detail with reference to FIG. 7.

The result output unit 160' outputs information of the original shape embodied through the shape analysis unit 150'.

In this case, the result output unit 160' may output the restored shape as display information that can be identified, such that a user (e.g., a subject) can identify the information with the naked eyes or through listening. For example, the result output unit 160' may output the shape imagined by the user on the screen of the display 110'.

In addition, the result output unit 160' may transfer a signal including information of the embodied original shape to a pre-cooperated related device. For example, a brain-machine interface apparatus 100' in accordance with another example embodiment may be equipped in a remote control of a home appliance like a TV. That is, the display 110' may be equipped as a small liquid display in a remote control, and the line arrangement where the multiple light-emitting lines are flickering may be output on the small liquid display. In this case, if a user imagines his/her intended shape (i.e., a letter, a numeral, a symbol, etc.) in the state that he/she watches the line arrangement on the small liquid display of the remote control, the original shape is analyzed and restored through analysis of EEG of the user and transferred to an incorporated related device. In this way, the user may perform preset operations through related equipment by only imagining a shape associated with a certain command. For example, it is assumed to watch a remote control equipped with at least one component including the display 110' of the brain-machine interface apparatus 100'. In this case, if the user imagines the letters 'A,' 'B,' and 'C' in this order, the brain-machine interface apparatus 100' may restore the shape of "ABC" through EEG analysis. In this case, in order to enable a TV channel in response to the letter information of the restored "ABC" to be automatically selected, the result output unit 160' may transmit a signal including the corresponding information to a preset related device (i.e., a receiving device of a TV). For reference, the brain-machine interface apparatus 100' may also be equipped in a smart device like a smart phone. In this case, it is also possible to transfer information of the original shape embodied according to a user's EEG signals to a preset application (i.e., software) so as to perform preset operations or processes.

Hereinafter, the configuration and operation of the shape analysis unit 150' is described in detail with reference to FIG. 7.

FIG. 7 describes a process for analyzing and embodying an original shape imagined by a subject using an EEG signal through a brain-machine interface apparatus in accordance with another example embodiment.

As illustrated in FIG. 7, the shape analysis unit 150' may include a classifier 151 or be the classifier 151 itself. The classifier 151 generates one or more EEG features detected from a labeled training EEG signal through preset machine learning processing. For example, the classifier 151 may be generated through either supervised machine learning or unsupervised machine learning. For reference, EEG features detected from a training EEG signal are frequency components.

Prior to performing procedures for analyzing a user's EEG signals to embody an original shape imagined by the user, the shape analysis unit 150' performs initial processing for labeling an EEG signal related to a multiple number of reference shapes. For reference, the reference shapes mean any types of shapes, letters, numerals, symbols and others that can be generated by the combination of the individual light-emitting lines embedded in the grid-shaped line arrangement.

First, the light-emitting lines flickering at its own individual flickering frequencies are output on the screen of the display 110'. In the state that a subject already intend (or conceive) a specific shape (i.e., a reference shape), its corresponding EEG features (e.g., SSVEPs) of the subject are measured through the EEG measurement unit 130'. Accordingly, EEG signals measured for the shapes (i.e., the already known shapes) imagined by the subject are measured by the frequency detector 140'. The frequency detector 140' makes the detected EEG signals subject to Fast Fourier Transform, to extract feature components thereof. In this case, since the EEG signals processed through the frequency detector 140' are related to the already known shapes, they are labeled training EEG signals. The EEG feature components (i.e., frequency components) detected through the extraction of the features by the frequency detector 140' are input and stored in the shape analysis unit 150'.

The shape analysis unit 150' performs machine learning (e.g., supervised or unsupervised machine learning) for the frequency aspects detected from the labeled EEG signals to process calibration for setting a standard value of the classifier 151. Accordingly, when receiving input of frequencies according to an EEG signal of a subject later, the classifier 151 classifies and outputs a shape matched with the input frequencies according to the EEG signal. This classifier 151 may use a multi-class vector machine like a support vector machine.

As described above, prior to restoring the original shape imagined by a subject, machine learning for the labeled EEG signals for the multiple reference shapes is performed as preprocessing.

Thereafter, as illustrated in FIG. 7, the frequency detector 140' receives input of an EEG signal newly measured from the subject through the EEG measurement unit 130'. That is, the frequency detector 140' receives input of an untraining (or testing) EEG trial signal. FIG. 7 illustrates an example for the case where a subject imagines the shape "T" P20 in the state that the subject watches the line arrangement P10 output on the screen of the display 110'. Accordingly, the frequency detector 140' extracts, from the newly measured EEG signal, feature frequencies including flickering frequencies of light-emitting lines corresponding to the shape "T" among the lines output on the line arrangement P10.

In addition, the shape analysis unit 150' receives input of flickering frequencies of the two light-emitting lines corresponding to the shape "T" and a frequency combination of the flickering frequencies from the frequency detector 140'. Thereafter, the shape analysis unit 150 classifies the shape matched with the corresponding frequencies through the classifier 151. As a result, as illustrated in FIG. 7, the shape "T" P30 corresponding to the detected frequencies among the multiple reference shapes are classified through the classifier 151. The shape analysis unit 150' embodies (or decodes) the shape "T" according to the classification result of the classifier 151 as an original shape.

For reference, if there is no reference shape exactly corresponding to the frequencies detected through the frequency detector 140', the shape analysis unit 150' may combine shapes of the individual lines corresponding to the detected frequencies to estimate and restore a specific shape. In this case, the shape analysis unit 150' may detect a reference shape having the highest similarity to the restored shape among the multiple reference shapes to embody the reference shape as the originally intended shape.

Hereinafter, a brain-machine interface method in accordance with another example embodiment is described in detail with reference to FIG. 8.

FIG. 8 is a flow diagram for describing a brain-machine interface method in accordance with another example embodiment.

First, a line arrangement consisting of two or more light-emitting lines that flicker with their respective set frequencies is output on the screen of the display 110' (S810).

In this case, the line arrangement may be designed in the form where the two or more light-emitting lines are arranged in a grid form.

Next, the two or more light-emitting lines included in the line arrangement are controlled to flicker with individually different frequencies (S820).

In this case, a difference of bandwidths of frequencies by rows and columns on the line arrangement may be set to be a reference value or more.

Next, an EEG signal of a user who watches the line arrangement output on the screen of the display 110' is measured (S830).

In this case, a steady state visual evoked potential (SS-VEP) may be measured as the EEG signal.

Next, at least one frequency component is detected from the measured EEG signal (S840).

In this case, one or more individual frequencies and a combined (or harmonic) frequency of the two or more individual frequencies are detected from the EEG signal. For example, a user's EEG signals may be subject to feature extraction processing through Fast Fourier Transform to detect one or more frequencies.

Next, preset pattern recognition processing for the detected frequencies is performed to restore and embody (or decode) the originally intended shape imagined by the subject (S850).

In this case, it is possible to use a classifier generated by having the labeled training EEG signal for the already known reference shapes be subject to machine learning processing. Specifically, prior to S850 for restoring the original shape, a classifier is generated by having one or more frequencies detected from a labeled training EEG signal for a specific shape be subject to machine learning processing. In addition, one or more frequencies detected from the EEG signal (i.e., untraining (testing) EEG signal) of a subject as measured in S840 are pattern-recognized through the classifier to classify a corresponding shape. In this way, the originally intended shape imagined by a subject may be restored from the EEG signal of the subject.

Thereafter, the decoded information of the originally intended shape is output (S860).

In this case, the originally intended shape may be output as display information including at least one of a letter, a numeral, and a symbol, or a signal including information of the original shape may be transmitted to a pre-cooperated related device.

Example embodiments can be embodied in a storage medium including instruction codes executable by a computer or processor such as a program module executed by the computer or processor. A computer readable medium can be any usable medium which can be accessed by the computer and includes all volatile/nonvolatile and removable/non-removable media. Further, the computer readable medium may include all computer storage and communication media. The computer storage medium includes all volatile/nonvolatile and removable/non-removable media embodied by a certain method or technology for storing information such as computer readable instruction code, a data structure, a program module or other data. The communication medium typically includes the computer readable instruction code, the data structure, the program module, or other data of a modulated data signal such as a carrier wave, or other transmission mechanism, and includes information transmission mediums.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

I claim:

1. A brain-machine interface apparatus comprising:
    a display configured to output a light signal from a plurality of light-emitting devices included in the display in a grid-like arrangement and flickering with their set frequencies, wherein:
        the plurality of light-emitting devices are divided into a plurality of subsets, each subset comprising at least two light-emitting devices, and
        the light-emitting devices of each of the plurality of subsets are arranged adjacent to a plurality of crosspoints of an imaginary matrix shape, on the display, that comprises a plurality of rows and a plurality of columns, wherein each of the plurality of rows intersects with each of the plurality of columns at said cross points;
    a flickering controller configured to divide the plurality of the light-emitting devices into a plurality of groups, and assign set frequencies for each of the plurality of groups;
    an EEG (Electroencephalogram) measurement unit configured to measure an EEG signal of a user who watches an output of the display,
    wherein the user imagines a shape while watching the output of the display, and
    wherein the shape imagined by the user is selected from a group consisting of shapes, letters, numerals, or symbols and that can be generated by the combination of one or more of the plurality of light-emitting devices;
    a frequency detector that is configured to detect one or more frequency components from the EEG signal;
    a processor; and
    a non-transitory, computer-readable memory containing programming instructions that are configured to cause the processor to:

determine one or more groups of light-emitting devices from among the plurality of groups of light-emitting devices corresponding to one or more frequency components detected from an EEG signal of a user watching an output of the display, determine one or more arrangement forms associated with the determined one or more groups of light-emitting devices, determine a shape imagined by the user while watching the output of the display based on the one or more arrangement forms, and output information corresponding to the shape imagined by the user.

2. The brain-machine interface apparatus of claim 1, wherein the flickering controller is configured to divide the plurality of light-emitting devices into the plurality of groups by assigning each of at least two light-emitting devices of each subset of light-emitting devices into different ones of the plurality of groups.

3. The brain-machine interface apparatus of claim 2, wherein the flickering controller is configured to divide the plurality of the light-emitting devices into the plurality of groups, and assign set frequencies for each of the plurality of groups based on one or more of the following:

divide the plurality of light-emitting devices into the plurality of groups such that each of the plurality of groups comprises light-emitting devices arranged along one of the plurality of rows of the imaginary matrix and a difference in bandwidth between set frequencies corresponding to adjacent rows of the plurality of rows is equal to or greater than a predetermined value;

divide the plurality of light-emitting devices into the plurality of groups such that each of the plurality of groups comprises light-emitting devices arranged along one of the plurality of columns of the imaginary matrix and a difference in bandwidth between set frequencies corresponding to is equal to or greater than a predetermined value; and divide the plurality of light-emitting devices into the plurality of groups such that each of the plurality of groups comprises light-emitting devices arranged along one of the plurality of rows of the imaginary matrix or along one of the plurality of columns of the imaginary matrix, and a sum of set frequencies corresponding to a combination of set frequencies corresponding to one row and one column is different from a sum of frequencies corresponding to a combination of set frequencies corresponding to another row and another column.

4. The brain-machine interface apparatus of claim 2, wherein the flickering controller is further configured to divide the plurality of light-emitting devices into the plurality of groups according to preset positions and ranges on the imaginary matrix feffn shape.

5. The brain-machine interface apparatus of claim 1, wherein the programming instructions further comprise instructions that cause the processor to:

determine one or more groups of light-emitting devices from among the plurality of groups of light-emitting devices by identifying at least one group from among the plurality of groups of light-emitting devices for which the set frequency corresponds to the one or more detected frequency components;

determine the one or more arrangement forms by identifying an arrangement of light emitting devices included in the at least one group; and determine the shape imagined by the user while watching the output of the display based on the one or more arrangement forms by:

identifying a first shape based on the one or more arrangement forms; and determining that the shape imagined by the user is one or more of the following: the first shape, or a reference having the highest similarity to the first shape among a plurality of pre-stored reference shapes.

6. The brain-machine interface apparatus of claim 2, wherein the programming instructions further comprise instructions that cause the processor to:

measure a maximum visual angle and an effective visual angle at a distance of preset spacing from the display when a user focuses toward the display is maintained, and select light-emitting devices to be activated from the plurality of light-emitting devices based on the measured maximum visual angle and effective visual angle, wherein the flickering controller is configured to control the light-emitting devices.

7. The brain-machine interface apparatus of claim 2, wherein the plurality of light-emitting devices include at least one type of light-emitting devices among red, green and white light emitting diodes (LEDs).

8. The brain-machine interface apparatus of claim 1, wherein the EEG measurement unit is configured to measure a steady state visual evoked potential (SSVEP).

9. The brain-machine interface apparatus of claim 1, wherein the programming instructions that are configured to cause the processor to output information corresponding to the shape imagined by the user further comprise programming instructions to:

output the shape imagined by the user as display information including at least one of a shape, a letter, a numeral and a symbol that can be identified, or output a signal including the information of the shape imagined by the user to a pre-cooperated related device.

10. The brain-machine interface apparatus of claim 1, wherein the frequency detector is configured to detect one or more individual frequencies and a combined frequency of two or more individual frequencies from the EEG signals.

11. A brain-machine interface method, the method comprising:

generating, by a plurality of light emitting devices on a display of a brain machine interface apparatus, an output light signal, wherein:

the plurality of light-emitting devices are divided into a plurality of subsets, each subset comprising at least two light-emitting devices, and the light-emitting devices of each of the plurality of subsets are arranged adjacent to a plurality of crosspoints of an imaginary matrix shape, on the display, that comprises a plurality of rows and a plurality of columns, wherein each of the plurality of rows intersects with each of the plurality of columns at said cross points;

dividing the plurality of light-emitting devices into a plurality of groups by assigning each of at least two light-emitting devices of each subset of light-emitting devices into different ones of the plurality of groups;

controlling the plurality of groups to flicker at different set frequencies;

measuring an EEG (Electroencephalogram) signal of a user who watches the output on the display and imagines a shape while watching the output, wherein the shape imagined by the user is selected from a group consisting of shapes, letters, numerals, or symbols and that can be generated by the combination of one or more of the plurality of light-emitting devices, and;

detecting one or more frequency components from the measured EEG signal;

identifying information corresponding to the shape imagined by the user based on the one or more detected frequency components and the set frequencies; and outputting the information corresponding to the shape imagined by the user.

12. The brain-machine interface method of claim 11, wherein:

identifying the information corresponding to the shape imagined by the user comprises determining one or more arrangement forms corresponding to the one or more frequency components by:

identifying at least one group from among the plurality of groups for which the set frequency corresponds to the one or more detected frequency components, and identifying an arrangement of light emitting devices included the at least one group, wherein the one or more arrangement forms are associated with the plurality of groups of light-emitting devices; and identifying information corresponding to the shape imagined by the user based on the one or more detected frequency components and the set frequencies by:

identifying a first shape based on the one or more arrangement forms, and determining that the shape imagined by the user is one or more of the following: the first shape, or a reference having the highest similarity to the first shape among a plurality of pre-stored reference shapes.

13. The brain-machine interface method of claim 11, wherein a steady state visual evoked potential (SSVEP) is measured as a user's EEG signals.

14. A brain-machine interface apparatus comprising:

a display configured to output a light signal from a plurality of light-emitting devices included in the display in a grid-like arrangement and flickering with their set frequencies, wherein:

the plurality of light emitting devices are arranged in a grid form comprising a plurality of row lines and a plurality of column lines that intersect each other;

a flickering controller configured to control each of the plurality of row lines and each of the plurality of column lines to flicker at different set frequencies;

an EEG (Electroencephalogram) measurement unit configured to measure an EEG signal of a user who watches an output of the display, wherein the user imagines a shape while watching the output of the display, and wherein the shape imagined by the user is selected from a group consisting of shapes, letters, numerals, or symbols and that can be generated by the combination of one or more of the plurality of light-emitting devices;

a frequency detector that is configured to detect one or more frequency components from the EEG signal;

a processor; and a non-transitory, computer-readable memory containing programming instructions that are configured to cause the processor to:

determine one or more groups of light-emitting devices from among the plurality of row lines and column lines corresponding to one or more frequency components detected from an EEG signal of a user watching an output of the display, determine one or more arrangement forms associated with the determined one or more groups of light-emitting devices, determine a shape imagined by the user while watching the output of the display based on the one or more arrangement forms, and output information corresponding to the shape imagined by the user.

15. The brain-machine interface apparatus of claim 14, wherein the grid form consists of three row lines and three column lines, which flicker at different set frequencies.

16. The brain-machine interface apparatus of claim 14, wherein the flickering controller is further configured to set a difference in bandwidth between the set frequencies for the row lines and the column lines of the grid form to be a equal to or greater than a predetermined value.

17. The brain-machine interface apparatus of claim 14, wherein the programming instructions further comprise instructions to:

perform preset pattern recognition processing for the one or more detected frequency components to classify the EEG features; and determine the classified shape as the shape imagined by the user.

18. The brain-machine interface apparatus of claim 14, wherein the programming instructions further comprise instructions to:

generate a classifier through machine learning processing for one or more frequency components detected from a training EEG signal labeled in advance for a certain shape, and using the classifier match a shape with the one or more detected frequency components detected from a user's EEG signals.

* * * * *